United States Patent
Koizumi et al.

(10) Patent No.: US 10,632,177 B2
(45) Date of Patent: Apr. 28, 2020

(54) MYOBLAST DIFFERENTIATION PROMOTER

(71) Applicant: NITTA GELATIN INC., Osaka (JP)

(72) Inventors: Seiko Koizumi, Osaka (JP); Fumihito Sugihara, Osaka (JP); Naoki Inoue, Osaka (JP)

(73) Assignee: NITTA GELATIN INC., Osaka-shi, Osaka (JP)

(*) Notice: Subject to any disclaimer, the term of this patent is extended or adjusted under 35 U.S.C. 154(b) by 336 days.

(21) Appl. No.: 15/299,172

(22) Filed: Oct. 20, 2016

(65) Prior Publication Data
US 2017/0035858 A1    Feb. 9, 2017

Related U.S. Application Data

(63) Continuation of application No. 14/382,700, filed as application No. PCT/JP2013/083324 on Dec. 12, 2013, now abandoned.

(30) Foreign Application Priority Data

Dec. 13, 2012   (JP) ................. 2012-272110

(51) Int. Cl.
| | | |
|---|---|---|
| *A61K 38/39* | (2006.01) | |
| *C07K 5/062* | (2006.01) | |
| *C07K 5/072* | (2006.01) | |
| *C07K 5/083* | (2006.01) | |
| *C07K 5/078* | (2006.01) | |
| *C07K 5/097* | (2006.01) | |
| *A23L 33/18* | (2016.01) | |
| *A23K 20/147* | (2016.01) | |
| *A61K 38/00* | (2006.01) | |

(52) U.S. Cl.
CPC ............ *A61K 38/39* (2013.01); *A23K 20/147* (2016.05); *A23L 33/18* (2016.08); *C07K 5/06026* (2013.01); *C07K 5/06043* (2013.01); *C07K 5/06104* (2013.01); *C07K 5/06165* (2013.01); *C07K 5/0806* (2013.01); *C07K 5/0808* (2013.01); *C07K 5/0823* (2013.01); *A61K 38/00* (2013.01)

(58) Field of Classification Search
CPC ......... A61K 38/39; A61K 38/00; A23L 33/18; A23K 20/147; C07K 5/06026; C07K 5/06104; C07K 5/06043; C07K 5/06165; C07K 5/0808; C07K 5/0806; C07K 5/0823
See application file for complete search history.

(56) References Cited

U.S. PATENT DOCUMENTS

| | | |
|---|---|---|
| 2005/0288229 A1 | 12/2005 | Sindrey et al. |
| 2011/0021590 A1 | 1/2011 | Duggan |
| 2011/0166365 A1* | 7/2011 | Sugihara ............... A61K 38/05 548/532 |
| 2012/0040055 A1 | 2/2012 | Ohara et al. |
| 2012/0156276 A1 | 6/2012 | Sindrey et al. |
| 2013/0303448 A1 | 11/2013 | Sugihara et al. |

FOREIGN PATENT DOCUMENTS

| | | |
|---|---|---|
| JP | 2002-255847 A | 9/2002 |
| JP | 2004-115438 A | 4/2004 |
| JP | 2006-502971 A | 1/2006 |
| JP | 2008-156294 A | 7/2008 |
| JP | 2010-024200 A | 2/2010 |
| JP | 2010-106003 A | 5/2010 |
| JP | 2013-227228 A | 11/2013 |
| WO | 2007/017671 A1 | 2/2007 |
| WO | 2009/035169 A1 | 3/2009 |
| WO | 2010/038323 A1 | 4/2010 |
| WO | 2010/125910 A1 | 11/2010 |
| WO | 2012/102308 A1 | 8/2012 |

OTHER PUBLICATIONS

Food Style 21, Sep. 2012, vol. 16, No. 9, 3 pp.
Japanese Patent Application No. 2014-552081, English translation of Office Action dated Apr. 3, 2018, 4 pp.
Iwasa et al. (2010) "[Effect of Marine Collagen Intake on Buildup of Bodies of Student American Football Players]," [Food Style]. 14(7):62-65.—with English translation.
Ogawa et al. (2011) "17β-Estradiol Represses Myogenic Differentiation by Increasing Ubiquitin-specific Peptidase 19 through Estrogen Receptor α," Journal of Biological Chemistry. 286(48):41455-41465.
Suzuki et al. (2011) "Creation of the Antioxidative Peptide Derived from Collagen," In; The Japanese Society for Amino Acid Sciences, The Fifth Academic Meeting (JSAAS2011) Abstracts. pp. 74.—with English translation.
Zammit et al. (2006) "The skeletal muscle satellite cell: the stem cell that came in from the cold," J. Histochem. Cytochem. 54(11):1177-1191.
International Search Report corresponding to International Patent Application No. PCT/JP2013/083324, dated Jan. 14, 2014.
Okiura et al. (2008) "[Verification of Effect of Improving Bone Density and Muscle Function of Chicken-Derived Collagen Hydrolysate Using Model Mouse Suffering from Senile Osteoporosis]," Amino Acid Research. 2(1):82.—Provided with a partial English translation.
Shigemura et al. (2008) "[Effect of Dietary-Derived Main Collagen Peptide (Pro-Hyp, Hyp-Gly) upon Mouse Skin Fibroblast Growth]," In; The The Japan Society for Bioscience, Biotechnology, and Agrochemistry, Kansai Branch, Lecture Meeting, Summary Report. 456:28. Abstract No. A07.—Provided with a partial English translation.

(Continued)

*Primary Examiner* — Sudhakar Katakam
(74) *Attorney, Agent, or Firm* — Sughrue Mion, PLLC

(57) ABSTRACT

A peptide selected from the group consisting of Ala-Hyp-Gly, Hyp-Gly-Pro, Leu-Hyp, Glu-Hyp, Gly-Pro-Hyp, Pro-Ala, Hyp-Gly and Pro-Hyp, or a pharmaceutically acceptable salt thereof has a myoblast differentiation promoting effect superior to conventional arts.

16 Claims, No Drawings

(56) References Cited

OTHER PUBLICATIONS

Yamamoto et al. (2012) "[Effect of Collagen-Derived Dipeptide Pro-Hyp upon Collagen Synthesis of Skeletal Muscle]," In; The Abstracts of the the 132nd Annual Meeting of the Pharmaceutical Society of Japan. 32(4):239. Abstract No. 30P2-am169.—with English translation.
Zolotarev et al. (2006) "Short Peptide Fragments with Antiulcer Activity form a Collagen Hydrolysate," Russian Journal of Bioorganic Chemistry. 32(2):174-178.
Office Action corresponding to Chinese Patent Application No. 201380022730.5, dated Sep. 22, 2017—with English translation.
Office Action corresponding to Japanese Patent Application No. 2014-552081, dated Sep. 5, 2017—with English translation.
Office Action corresponding to Japanese Patent Application No. 2014-552081, dated Apr. 3, 2018—with English translation.

\* cited by examiner

MYOBLAST DIFFERENTIATION PROMOTER

CROSS-REFERENCE TO RELATED APPLICATIONS

This application is a continuation of U.S. patent application Ser. No. 14/382,700, filed Sep. 3, 2014, which is a 35 U.S.C. 371 of PCT/JP2013/083324, filed Dec. 12, 2013, which claims priority to Japanese Patent Application No. 2012-272110, filed Dec. 13, 2012, the entire disclosures of which are hereby incorporated herein by reference.

TECHNICAL FIELD

The present invention relates to a myoblast differentiation promoter comprising peptide molecule(s) or the like.

BACKGROUND ART

Recently, prevention and the like of locomotive syndrome and sarcopenia (reductions in muscle quantity and muscle strength, and decrease in physical function) attract attentions, and it is demanded to ameliorate such symptoms by increases in muscle quantity and muscle strength. Also for healthy persons, prevention of muscular fatigue and enhancement of muscle are demanded.

In an initial process of muscle cell differentiation, an undifferentiated cell differentiates into a myoblast which is a cell derived from a muscle fiber. The myoblast further differentiates, and a protein that is specific to a muscle cell is expressed. A phenomenon characteristic of differentiation of a muscle cell is cell fusion, i.e., a phenomenon that myoblasts which are mononuclear cells fuse to differentiate into a myotube cell which is a multinucleate cell. Further, through a process of formation of a muscle fiber having a contracting ability from a matured myotube cell, muscle is completed. During the differentiation of myoblasts, characteristic proteins such as tropomyosin and myosin heavy chain are generated, and these are used as differentiation markers (Non-Patent Literature 1).

Peptide molecules are known to have various pharmacological effects. For example, Patent Literature 1 describes that dipeptides such as Hyp-Gly have an osteoclast differentiation inhibiting effect, an alkaline phosphatase inhibiting effect, and so on. Non-Patent Literature 2 describes that peptides such as Hyp-Gly-Pro have an antioxidative effect. Patent Literature 2 describes that peptides such as Pro-Gly and Hyp-Gly which further have up to ten amino acids in their upstream region and/or in their downstream region, have effects of stimulating growth, maintenance and repair of bone or the like.

Patent Literature 3 describes that *Rosa roxburghii*, a soybean peptide, a C12 peptide and the like have a myoblast activating effect. However, whether these peptide molecules have a myoblast differentiation promoting effect has not been known.

Non-Patent Literature 3 shows the rate of change in muscle weight when American football players took in an equivalent mixture of a collagen peptide and a whey peptide for three months in combination with exercise. Although the muscle weight increased (FIG. 2), the body weight also increased (FIG. 1) after intake of this equivalent mixture, and the muscle, in terms of a ratio of the muscle weight to the body weight, was rather reduced in comparison with the starting point. In contrast to this, in the present invention, the ratio of the muscle weight to the body weight significantly increases as described in later-described Test Example 2.

CITATION LIST

Patent Document

PTD 1: WO2010/038323
PTD 2: Japanese National Patent Publication No. 2006-502971
PTD 3: Japanese Patent Laying-Open No. 2008-156294

Non Patent Document

NPD 1 J. Biol. Chem., Vol. 286, No. 48, 41455 (2011)
NPD 2 The Japanese Society for Amino Acid Sciences, The fifth academic meeting (JSAAS2011), Abstracts, p. 74
NPD 3 Food Style 21, Vol. 14, No. 7, 62-65 (2010)

SUMMARY OF INVENTION

Technical Problem

It is an object of the present invention to provide a myoblast differentiation promoter comprising peptide molecule(s), that is superior to conventional arts.

Solution to Problem

As a result of diligent efforts, the present inventors have found that peptide molecules Ala-Hyp-Gly, Hyp-Gly-Pro, Leu-Hyp, Glu-Hyp, Gly-Pro-Hyp, Pro-Ala, Hyp-Gly and Pro-Hyp have an excellent myoblast differentiation promoting effect, and have accomplished the present invention. Specifically, the present invention is as follows.

[1] A myoblast differentiation promoter comprising a peptide selected from the group consisting of Ala-Hyp-Gly, Hyp-Gly-Pro, Leu-Hyp, Glu-Hyp, Gly-Pro-Hyp, Pro-Ala, Hyp-Gly and Pro-Hyp, or a pharmaceutically acceptable salt thereof.

[2] The myoblast differentiation promoter according to [1], comprising a peptide selected from the group consisting of Hyp-Gly and Pro-Hyp, or a pharmaceutically acceptable salt thereof.

[3] The myoblast differentiation promoter according to [1], comprising two or more peptides selected from the group consisting of Ala-Hyp-Gly, Hyp-Gly-Pro, Leu-Hyp, Glu-Hyp, Gly-Pro-Hyp, Pro-Ala, Hyp-Gly and Pro-Hyp, or pharmaceutically acceptable salts thereof.

[4] The myoblast differentiation promoter according to any one of [1] to [3], wherein the promoter is in the form of a preparation for oral administration, an injection for direct administration to muscle, a transdermal agent, a suppository, a nasal drop, or an inhalant.

[5] A beverage or food product or a feed, comprising a peptide selected from the group consisting of Ala-Hyp-Gly, Hyp-Gly-Pro, Leu-Hyp, Glu-Hyp, Gly-Pro-Hyp, Pro-Ala, Hyp-Gly and Pro-Hyp, or a pharmaceutically acceptable salt thereof.

Advantageous Effects of Invention

The present invention can provide a myoblast differentiation promoter comprising a peptide molecule of Ala-Hyp-Gly, Hyp-Gly-Pro, Leu-Hyp, Glu-Hyp, Gly-Pro-Hyp, Pro-Ala, Hyp-Gly, and Pro-Hyp, that is superior to conventional arts.

DESCRIPTION OF EMBODIMENTS

Hereinafter, the present invention will be described in detail.

1. Peptide

Peptides used in the present invention are Ala-Hyp-Gly, Hyp-Gly-Pro, Leu-Hyp, Glu-Hyp, Gly-Pro-Hyp, Pro-Ala, Hyp-Gly and Pro-Hyp, and these peptides can be in the form of a pharmaceutically acceptable salt. Examples of preferred peptides include Hyp-Gly and Pro-Hyp.

Examples of the "pharmaceutically acceptable salt" include inorganic acid salts such as hydrochloride, sulfate and phosphate, organic acid salts such as methanesulfonate, benzenesulfonate, succinate and oxalate, inorganic basic salts such as a sodium salt, a potassium salt and a calcium salt, and organic basic salts such as a triethylammonium salt.

The present peptide can be synthesized, for example, by "a solid-phase synthesis method" and "a liquid-phase synthesis method" (for example, Japanese Patent Laying-Open No. 2003-183298). As the solid-phase synthesis method, a Fmoc method and a Boc method are known, and the present peptide may be synthesized in any of these methods. One example of the solid-phase synthesis method will be concretely described below. A bead of polystyrene polymer gel having a diameter of about 0.1 mm whose surface is modified with an amino group is used as a solid phase, and diisopropylcarbodiimide is used as a condensing agent. First, the amino group of C-terminal amino acid is protected with a Fmoc group or a Boc group, and allowed to form a peptide bond with the amino group of the aforementioned polystyrene polymer gel. The solid phase is washed well with a solvent to clean and remove the remaining reagent and amino acid, and then the protecting group of the amino group of the amino acid bound to the solid phase is removed. Subsequently, by sequentially repeating the same reaction using the amino acid whose amino group is protected, a peptide is synthesized on the solid phase. At last, the solid phase is digested in trifluoroacetic acid to detach the peptide from the solid phase, and thus the peptide can be synthesized.

The present peptide can also be produced by hydrolyzing gelatin with a combination of two or more kinds of endoprotease and exoprotease. Also, the peptide mixture itself obtained by above hydrolysis, or a mixture obtained by partial purification of the peptide mixture can be used as a myoblast differentiation promoter.

In the present invention, the present peptide may be chemically modified. Chemical modification can be carried out for an individual amino acid, for example, at the hydroxyl group of hydroxyproline, at the amino group of an N-terminal amino acid, and at the carboxyl group of a C-terminal amino acid. Such chemical modification enables dissolution under weak acidic to neutral conditions, and also allows improvement in compatibility with other active ingredient as described later.

Concretely, chemical modification at the hydroxyl group of hydroxyproline include, for example, O-acetylation. Chemical modification at the amino group of an N-terminal amino acid include, for example, polypeptidylation, succinylation, maleylation, acetylation, deamination, benzoylation, alkyl sulfonylation, allylsulfonylation, dinitrophenylation, trinitrophenylation, carbamylation, phenylcarbamylation, and thiolation are recited. Chemical modification at the carboxyl group of a C-terminal amino acid include, for example, esterification and amidation. When the present peptide is cationated, ethylenediamination, spermination, and so on can be carried out.

As to concrete measures and treatment conditions of chemical modification, a usual chemical modification technique for peptide is applied. For example, O-acetylation of the hydroxyl group of hydroxyproline can be achieved by allowing acetic anhydride to act in an aqueous solvent or in a nonaqueous solvent. For example, esterification of the carboxyl group of a C-terminal amino acid can be achieved, for example, by aeration with a dry hydrogen chloride gas following suspension in methanol, and amidation thereof can be achieved by allowing carbodiimide or the like to act on the same. Further, as other concrete examples of chemical modification, chemical modification techniques described in Patent Publication No. 62-44522 and Patent Publication No. 5-79046 can be applied.

2. Myoblast Differentiation Promoter

The present peptide or the like has a myoblast differentiation promoting effect as described in later-described Test Examples. Therefore, the present peptide or the like can be used for therapy or prevention of various diseases that require muscle enhancement. The myoblast differentiation promoter of the present invention can be used, for example, for therapy of locomotive syndrome, therapy of sarcopenia, improvement in the effect of training in athletes, students and so on, enhancement in physical strength of aged persons, long-stay inpatients and so on, and improvement in quality of meat of livestock.

The myoblast differentiation promoter of the present invention can be administered orally or parenterally in pharmaceutical preparations of various forms. Examples of the forms include tablet, granule, capsule, powder, liquid, suspension and emulsion for oral administration, and injection, transdermal agent, suppository, nasal drop and inhalant for parenteral administration. Preferred examples include tablet, granule, capsule, and liquid to be directly administered to a diseased site such as muscle. The present peptide is preferably taken in by oral administration because it is little digested into amino acids in the digestive tract, but is rapidly absorbed in the intestinal tract. The present peptide may be taken in while it is mixed with a meal or a beverage.

A dose of the present peptide varies depending on the condition or the body weight of the patient, the kind of the compound, the administration route and so on. In the case of oral administration per day for one adult, for example, about 0.1 to 1000 mg, preferably about 1 to 500 mg, and more preferably about 30 to 200 mg are recited, and in the case of direct administration to a diseased part such as muscle, for example, about 0.01 to 200 mg, preferably about 0.1 to 100 mg, and more preferably about 1 to 50 mg are recited. Doses of preparations of other forms can be appropriately determined with reference to these doses. These preparations can be administered daily in one to several divided doses, or may be administered once every one to several days.

The myoblast differentiation promoter of the present invention may appropriately comprise other active ingredient(s) and ingredient(s) for formulation as far as the effect of the present invention is not interfered. Examples of the other active ingredient include muscle-enhancing agents such as a male hormone, and muscle-enhancing supplements such as an amino acid mixture. Amounts of the other active ingredients formulated can be appropriately changed depending on the individual effects.

Examples of a pharmaceutically acceptable carrier used in preparation into a pharmaceutical preparation can include a diluent, a binder (syrup, gum arabic, gelatin, sorbit, tragacanth, polyvinylpyrrolidone), an excipient (lactose, sucrose, cornstarch, potassium phosphate, sorbit, glycine), a lubricant (magnesium stearate, talc, polyethylene glycol, silica), a disintegrant (potato starch) and a humectant (sodium lauryl sulfate). The present pharmaceutical preparation can be produced by mixing the present peptide(s), other active ingredient(s), a pharmaceutically acceptable carrier and so on according to conventionally known techniques.

3. Beverage or Food Product or Feed

Since the present peptide or the like is a peptide derived from gelatin, it is very safe for daily intake or application. Hence, it is also useful as a beverage or food product or a feed comprising the present peptide(s) or the like with the use of the excellent myoblast differentiation promoting effect of the present peptide(s) or the like. For example, the present invention can be used for enhancement in physical strength of aged persons, long-stay inpatients and so on, improvement in effect of training in athletes, students and so on, and improvement in quality of meat of livestock. The content of the present peptide(s) or the like used in a beverage or food product or a feed of the present invention can be varied appropriately depending on the effect to be utilized.

EXAMPLES

Hereinafter, the present invention will be described in more detail by Examples, Comparative Examples and Test Examples, but is not limited thereto in any way.

Examples 1 to 22 and Comparative Examples 1 to 4

Using the aforementioned peptide solid-phase synthesis method, the following peptides of Examples 1 to 8 and Comparative Example 1 were synthesized. Using these peptides, the following equivalent molar ratio mixtures of two kinds of peptides of Examples 9 to 21 were prepared, and the following equivalent molar ratio mixtures of two kinds of amino acids of Comparative Examples 2 and 3 were prepared. Also, the following commercially available collagen peptides of Example 22 and Comparative Example 4 were used.

(Example 1) Ala-Hyp-Gly (AOG)
(Example 2) Hyp-Gly-Pro (OGP)
(Example 3) Leu-Hyp (LO)
(Example 4) Glu-Hyp (EO)
(Example 5) Gly-Pro-Hyp (GPO)
(Example 6) Pro-Ala (PA)
(Example 7) Hyp-Gly (OG)
(Example 8) Pro-Hyp (PO)
(Example 9) Mixture of OG and PO (OG+PO)
(Example 10) Mixture of OG and AOG (OG+AOG)
(Example 11) Mixture of OG and OGP (OG+OGP)
(Example 12) Mixture of OG and LO (OG+LO)
(Example 13) Mixture of OG and EO (OG+EO)
(Example 14) Mixture of OG and GPO (OG+GPO)
(Example 15) Mixture of OG and PA (OG+PA)
(Example 16) Mixture of PA and AOG (PA+AOG)
(Example 17) Mixture of PA and OGP (PA+OGP)
(Example 18) Mixture of PA and LO (PA+LO)
(Example 19) Mixture of PA and EO (PA+EO)
(Example 20) Mixture of PA and GPO (PA+GPO)
(Example 21) Mixture of PA and PO (PA+PO)

(Example 22) Collagen peptide "Type-M (produced by Nitta Gelatin Inc.)"

As a result of LC-MS/MS analysis, this collagen peptide contained the following respective peptides.

Hyp-Gly: 7573 ppm, Pro-Ala: 2541 ppm, Ala-Hyp-Gly: 331 ppm, Pro-Hyp: 184 ppm, Gly-Pro-Hyp: 85 ppm, Glu-Hyp: 72 ppm, Hyp-Gly-Pro: 7 ppm (Comparative Example 1) Ala-Hyp (AO)
(Comparative Example 2) Mixture of Hyp and Gly (O+G)
(Comparative Example 3) Mixture of Pro and Hyp (P+O)
(Comparative Example 4) Collagen peptide "HDL-50SP (produced by Nitta Gelatin Inc.)"

As a result of LC-MS/MS analysis, this collagen peptide contained the following respective peptides.

Hyp-Gly: 11 ppm, Pro-Hyp: 8 ppm

Test Example 1

Myoblast Differentiation Promotion Test in Myoblast Culture

For culture of C2C12 myoblast derived from mouse, a D-MEM culture medium containing 10% FBS, 100 units/mL sodium penicillin G, 100 μg/mL streptomycin and 1.0 g/L NaHCO$_3$ (D-MEM culture medium (10% FBS, +P/S)) was used. Culture was conducted in an incubator at 37° C. containing 95% air and 5% CO$_2$. In the condition that C2C12 myoblast was 90% confluent, the culture medium was replaced by a D-MEM culture medium including 2% horse serum (HS), 100 units/mL sodium penicillin G, 100 μg/mL streptomycin and 1.0 g/L NaHCO$_3$ (D-MEM culture medium (2% HS+P/S)), and then the D-MEM culture medium (2% HS+P/S) replacement was repeated every two days to lead to differentiation into myotube cells. The peptides of Examples 1 to 21 and Comparative Examples 1 to 3 were added in a final concentration of 100 μM to the culture medium every the culture medium replacement, and cells were continuously exposed thereto for eight days.

The Western blotting method was conducted in the following procedure. The cells used for protein measurement were washed twice with PBS at the time of recovery, and the cells were scraped with a cell scraper and transferred to a tube, and centrifuged at 4° C. and at 250×g for 3 minutes, and then PBS was completely removed. For each tube, the cells were suspended in 100 μL of a buffer (20 mM HEPES-NaOH (pH 7.5), 0.5% NP-40, 1 mM EDTA, 100 μM AEBSF, 1 μg/mL aprotinin, 10 μg/mL leupeptin, 1 mM DTT, 1 mM sodium ortho-vanadate, 10 mM sodium fluoride, 10 μM ammonium molybdate, 10 mM sodium pyrophosphate), and then crushed under ice cooling for 5 seconds three times for each sample by using an ultrasonic disperser, followed by quantification of the amount of a protein. Quantification of the amount of a protein was conducted according to the method of Bradford using bovine serum albumin as a standard protein. After end of SDS-PAGE, a blotting device was used to conduct electro-transferring at 1.5 mA per 1 cm$^2$ of a membrane for 1 hour on a PVDF membrane equilibrated with methanol and subjected to pre-wetting by infiltration with a transfer buffer (48 mM Tris, 39 mM glycine). After end of the transferring, the PVDF membrane was blocked with PBS (−) containing 6% skim milk for 1 hour. A primary antibody was diluted in the following manner, and an antigen-antibody reaction was conducted overnight at 4° C. A peroxidase-conjugated secondary antibody against each primary antibody was diluted in PBS (−) containing 6% skim milk in the ratios: mouse anti-myosin heavy chain monoclonal antibody (MF20) culture supernatant ½000, mouse anti-tropomyosin monoclonal antibody (CH1) culture supernatant ½000, rabbit anti-GAPDH polyclonal antibody ⅓000, peroxidase-conjugated anti-mouse IgG ⅕000, and peroxidase-conjugated anti-rabbit IgG 1/2000, allowed to react for 30 minutes, and washed three times with PBS (−) for 10 minutes. Then the membrane was immersed in Immobilon™ Western Chemiluminescent HRP Substrate for 3 minutes, and detected by LAS-4000 (GE Healthcare, Buckinghamshire, UK). A band was converted into numbers by imageJ, and expressed in a numerical value in relation to 100 which was the value of the control. The result of the test for myoblast differentiation promotion is shown in Table 1.

TABLE 1

|  | Control | Tropomyosin 100 | Myosin heavy chain 100 |
|---|---|---|---|
| Example 1 | AOG | 191 | 218 |
| Example 2 | OGP | 181 | 166 |
| Example 3 | LO | 195 | 143 |
| Example 4 | EO | 140 | 214 |
| Example 5 | GPO | 165 | 217 |
| Example 6 | PA | 169 | 131 |
| Example 7 | OG | 419 | 334 |
| Example 8 | PO | 307 | 278 |
| Example 9 | OG + PO | 715 | 613 |
| Example 10 | OG + AOG | 615 | 550 |
| Example 11 | OG + OGP | 610 | 525 |
| Example 12 | OG + LO | 623 | 509 |
| Example 13 | OG + EO | 586 | 541 |
| Example 14 | OG + GPO | 597 | 539 |
| Example 15 | OG + PA | 613 | 407 |
| Example 16 | PA + AOG | 473 | 339 |
| Example 17 | PA + OGP | 454 | 321 |
| Example 18 | PA + LO | 451 | 301 |
| Example 19 | PA + EO | 442 | 343 |
| Example 20 | PA + GPO | 439 | 328 |
| Example 21 | PA + PO | 449 | 322 |
| Comparative Example 1 | AO | 44 | 62 |
| Comparative Example 2 | O + G | 7 | 87 |
| Comparative Example 3 | P + O | 1 | 95 |

As described in Non-Patent Literature 1, tropomyosin and myosin heavy chain are used as myoblast differentiation markers. The above test results demonstrated that in the test of each peptide of Examples 1 to 8, larger quantities of tropomyosin and myosin heavy chain that are myoblast differentiation markers are generated in comparison with the control. Therefore, it is understood that these peptides have a myoblast differentiation promoting effect.

It was revealed that peptide mixtures comprising two kinds of peptides selected from Ala-Hyp-Gly, Hyp-Gly-Pro, Leu-Hyp, Glu-Hyp, Gly-Pro-Hyp, Pro-Ala, Hyp-Gly and Pro-Hyp have a synergistic myoblast differentiation promoting effect. In particular, the mixture of Hyp-Gly and Pro-Hyp in Example 9 exhibited a significant myoblast differentiation promoting effect. The mixtures of only amino acids in Comparative Examples 2 and 3 did not exhibit the similar effect, revealing that the myoblast differentiation promoting effect first arises with the mixture of Pro-Hyp and Hyp-Gly as peptide molecules.

Test Example 2
Clinical Test

A clinical test was conducted using the collagen peptides of Example 22 and Comparative Example 4 as test collagen peptides. Subjects were 34 healthy women who were not athletes, aged 24 to 61. They were randomly assigned to a group taking in the collagen peptide of Example 22 (17 persons) and a group taking in the collagen peptide of Comparative Example 4 (17 persons), and a double blind test was conducted. They continuously took in 5 g per day of respective collagen peptides for 10 weeks. For evaluation, the muscle weight (kg: containing water content) of each subject was measured using TANITA body composition monitor right and left regional inner scan 50V BC-622-BK. Also, the water content (kg) measured at the same time was taken away, and a rate of muscle weight (%) per body weight was calculated and evaluated. The result is shown in Table 2 by mean value±standard deviation. The mark ** in the table means significance with P<0.001 with respect to Comparative Example 4 in Two-way-ANOVA.

TABLE 2

|  | Starting point (%) | After 10 weeks (%) |
|---|---|---|
| Example 22 | 16.07 ± 3.68 | 22.19 ± 4.08** |
| Comparative Example 4 | 16.10 ± 3.08 | 16.71 ± 3.99 |

As shown in Table 2, the peptide mixture abundantly comprising Hyp-Gly, Pro-Ala, Pro-Hyp and so on, hydrolyzed with a specific enzyme (Example 22), exhibited significant effectiveness in muscle weight percentage in comparison with the peptide mixture hydrolyzed with a conventionally-known ordinary enzyme (Comparative Example 4).

INDUSTRIAL APPLICABILITY

The present invention is able to provide a myoblast differentiation promoter comprising peptide(s) derived from natural collagen, that is superior to conventional arts.

The invention claimed is:

1. A method for promoting myoblast differentiation in a subject in need thereof, comprising administering to the subject a mixture of peptides selected from the group consisting of Hyp-Gly and Ala-Hyp-Gly, Hyp-Gly and Hyp-Gly-Pro, Hyp-Gly and Leu-Hyp, Hyp-Gly and Glu-Hyp, Hyp-Gly and Gly-Pro-Hyp, Hyp-Gly and Pro-Ala, Pro-Ala and Ala-Hyp-Gly, Pro-Ala and Hyp-Gly-Pro, Pro-Ala and Leu-Hyp, Pro-Ala and Glu-Hyp, Pro-Ala and Gly-Pro-Hyp, and Pro-Ala and Pro-Hyp, or a pharmaceutically acceptable salt thereof, such that myoblast differentiation is achieved.

2. The method according to claim 1, wherein the mixture is administered to the subject in the form of a preparation for oral administration, an injection for direct administration to muscle, a transdermal agent, a suppository, a nasal drop, or an inhalant.

3. The method according to claim 1, wherein the promoting myoblast differentiation comprises treating locomotive syndrome, sarcopenia, improving the effect of training, enhancing physical strength of aged persons or long-stay inpatients, or improving the quality of livestock.

4. The method according to claim 1, wherein the dose of the mixture per day for one adult is about 1 to 1000 mg in the case of oral administration, and about 0.01 to 200 mg in the case of direct administration to a diseased part.

5. The method according to claim 1, wherein the mixture is administered with other active ingredient(s) and/or ingredient(s) for formulation.

6. The method according to claim 1, wherein the mixture comprises Hyp-Gly and Pro-Ala, or a pharmaceutically acceptable salt thereof.

7. The method according to claim 3, wherein the promoting myoblast differentiation comprises treating sarcopenia.

8. A method for promoting myoblast differentiation in a subject in need thereof, comprising administering to the subject a mixture of peptides comprising Hyp-Gly, Pro-Ala, Ala-Hyp-Gly, Pro-Hyp, Gly-Pro-Hyp, Glu-Hyp, and Hyp-Gly-Pro, such that myoblast differentiation is achieved.

9. The method according to claim 8, wherein the peptide is administered to the subject in the form of a preparation for oral administration, an injection for direct administration to muscle, a transdermal agent, a suppository, a nasal drop, or an inhalant.

10. The method according to claim 8, wherein the promoting myoblast differentiation comprises treating locomotive syndrome, sarcopenia, improving the effect of athletic training, enhancing the physical strength of aged persons or long-stay inpatients, or improving the quality of livestock.

11. The method according to claim 8, wherein the dose of the mixture per day for one adult is about 1 to 1000 mg for oral administration, and about 0.01 to 200 mg for direct administration to a diseased part.

12. The method according to claim 8, wherein the mixture is administered with other active ingredient(s) and/or ingredient(s) for formulation.

13. The method according to claim 10, wherein the promoting myoblast differentiation comprises treating sarcopenia.

14. The method of claim 8, wherein the concentration of Hyp-Gly is about 7573 parts per million (ppm), the concentration of Pro-Ala is about 2541 ppm, the concentration of Ala-Hyp-Gly is about 331 ppm, the concentration of Pro-Hyp is about 184 ppm, the concentration of Gly-Pro-Hyp is about 85 ppm, the concentration of Glu-Hyp is about 72 ppm, or the concentration of Hyp-Gly-Pro is about 7 ppm.

15. The method of claim 8, wherein the concentration of Hyp-Gly is about 7573 parts per million (ppm), the concentration of Pro-Ala is about 2541 ppm, the concentration of Ala-Hyp-Gly is about 331 ppm, the concentration of Pro-Hyp is about 184 ppm, the concentration of Gly-Pro-Hyp is about 85 ppm, the concentration of Glu-Hyp is about 72 ppm, and the concentration of Hyp-Gly-Pro is about 7 ppm.

16. The method of claim 8, wherein myoblast differentiation is measured by the change in percent (%) muscle weight to individual body weight over the period of administration of the mixture of peptides.

\* \* \* \* \*